(12) United States Patent
DuBourdieu et al.

(10) Patent No.: US 8,865,770 B2
(45) Date of Patent: Oct. 21, 2014

(54) CARBAMIDE PEROXIDE TREATMENTS FOR THE REPRODUCTIVE TRACT

(75) Inventors: Daniel J. DuBourdieu, Limerick, ME (US); Raj Lall, Menomonie, WI (US)

(73) Assignee: Vets Plus, Inc., Knapp, WI (US)

( * ) Notice: Subject to any disclaimer, the term of this patent is extended or adjusted under 35 U.S.C. 154(b) by 246 days.

(21) Appl. No.: 13/022,156

(22) Filed: Feb. 7, 2011

(65) Prior Publication Data

US 2012/0178816 A1    Jul. 12, 2012

Related U.S. Application Data

(60) Provisional application No. 61/430,433, filed on Jan. 6, 2011.

(51) Int. Cl.
| | | |
|---|---|---|
| *A01N 47/28* | (2006.01) | |
| *A61K 31/17* | (2006.01) | |
| *A61K 31/232* | (2006.01) | |
| *A61K 45/06* | (2006.01) | |

(52) U.S. Cl.
CPC .............. *A61K 31/17* (2013.01); *A61K 31/232* (2013.01); *A61K 45/06* (2013.01)
USPC ........................................ 514/588

(58) Field of Classification Search
None
See application file for complete search history.

(56) References Cited

U.S. PATENT DOCUMENTS

| | | | |
|---|---|---|---|
| 3,196,074 A | 7/1965 | Huffman | |
| 3,903,265 A | 9/1975 | Meisch | |
| 4,726,948 A * | 2/1988 | Prieels et al. | ............... 424/94.4 |
| 4,935,248 A | 6/1990 | Witkin | |
| 5,846,567 A | 12/1998 | Kalloo et al. | |
| 6,361,320 B2 * | 3/2002 | Yarborough | ................. 433/215 |
| 6,939,336 B2 | 9/2005 | Silfver | |

OTHER PUBLICATIONS

Clifford et al., *Hydrogen peroxide mediated killing of bacteria*, Molecular and Cellular Biochemistry 49, 143-149 (1982).
Dolezel, et al., *Bacterial contamination of the uterus in cows with various clinical types of metritis and endometritis and use of hydrogen peroxide for intrauterine treatment*, Veterinarni Medicina 55, (10) 504-511 (2010).
Gill et al., *Economics of Mastitis Control*, J. Dairy Sci, 73:3340-3348 (1990).
Overton, *Economics of Postpartum Uterine Health*, Proceedings of the 2008 Dairy Cattle Reproduction Council Convention, Nov. 2008, Omaha, Nebraska.
Weinstein et al., *The Action of Urea and Some of its Derivatives on Bacteria: I. Bacteriostatic and Bactericidal Effects of Urea and Urethane*, The Journal of Immunology, 54; 117-130 (1946).

* cited by examiner

*Primary Examiner* — Anna Pagonakis
(74) *Attorney, Agent, or Firm* — Daniel A. Blasiole; Charles S. Sara, Esq.; DeWitt Ross & Stevens S.C.

(57) ABSTRACT

Disclosed are methods of maintaining fertility or treating retained placenta, reproductive tract infection, or reproductive tract inflammation in an animal by administering carbamide peroxide to the reproductive tract of the animal. The carbamide peroxide administration removes placental remains on the uterine wall, protects against or treats reproductive tract infection, and protects against or treats reproductive tract inflammation such as metritis, and thereby maintains fertility in the animal.

12 Claims, No Drawings

CARBAMIDE PEROXIDE TREATMENTS FOR THE REPRODUCTIVE TRACT

CROSS-REFERENCE TO RELATED APPLICATIONS

This application claims priority under 35 USC §119(e) to U.S. Provisional Patent Application 61/430,433 filed Jan. 6, 2011, the entirety of which is incorporated herein by reference.

FIELD OF THE INVENTION

This invention relates to proteolytic and antimicrobial treatments of the reproductive tract of an animal for reducing reproductive failure resulting from metritis or other conditions.

BACKGROUND

The first week immediately after the birth of a calf is very crucial to the continued health of a mother cow and subsequent reproduction success. Up to 90% of dairy cows have bacterial contamination of the uterus in the first week postpartum. Normally, postpartum cows remove bacteria within six weeks by natural processes. However, complications such as sustained uterine infection, reproductive tract inflammation, or retained placenta can have a major impact on milk production or subsequent reproduction. Such complications and their effects can occur quite frequently. The risk of one type of reproductive tract inflammation, metritis, is around 22% in a typical herd. Predisposing factors are dystocia and retained fetal membranes, as well as deficiencies in hygiene and metabolic imbalances around parturition.

Metritis is probably the most economically important postpartum disorder in dairy cattle, causing high economic losses due to prolonged days open and involuntary culling. Metritis can result in an increase of open days (33 days), lower milk yield (typical loss of $83 per cow), and a decrease in pregnancy from a 17.5% normal rate to 13% with metritis. Together, these contribute to an average estimated annual cost of about $380 per cow. For a typical 1000-cow herd in 2008, metritis is estimated as costing $79,000 in losses due to milk loss, culling risk, and reproductive changes (Overton, M. and Fetrow J. *Proceedings* of the 2008 Dairy Cattle Reproduction Council Convention, Nov. 7-8, 2008, Omaha, Nebr.).

Metritis is an inflammation of the uterus and is often associated with malodorous watery uterine discharge and high (~103° F.) fever. Among other factors, infection with a number of infectious microorganisms plays a role in postpartum metritis. Metritis can present clinically or subclinically. Both clinical and subclinical metritis can have effects on milk production and fertility and, therefore, need to be avoided if possible.

For the farmer, there is a dilemma whether or not to treat cows for possible metritis. A variety of treatment therapies are available with varying success rates and varying costs associated with them. Intrauterine antibiotic therapy is one method. One of the most common antibiotics used is oxytetracycline. However, oxytetracycline treatment shows only limited efficacy and results in antibiotic residues appearing in milk. Prostaglandin (PGF) therapy shows some efficacy but is not economical. Iodine infusion is relatively inexpensive but can adversely affect subsequent reproduction. As such, all of these treatments have issues associated with them.

Successful cleansing of the postpartum cow is a major key to subsequent reproductive status and milk production. The lining of the postpartum uterus is in constant contact with fluid and tissue debris. This fluid and tissue debris can lead to growth with a variety of bacteria and other microorganisms. Whether or not infection develops in the uterus depends on the types of bacteria present and the condition of uterus. The uterus acts as an incubator as far as encouraging the rapid growth and increase in bacteria. The multiplication of bacteria is enhanced by sections of placenta that may cling to the uterine lining after calving. These fragments, sometimes small and sometimes quite large, may resist dislodgement by virtue of various cotyledons that have not released themselves. Cotyledons are button-like attachments that serve as the means for supplying nutrients from the mother cow to the fetus within the uterus. Before birth, the cotyledons range from 80 to 120 in number. In typical circumstances, most cotyledons dislodge during parturition. It is only those that do not release that prove troublesome, as they may retain sections of the placenta. When pieces of attached placenta remain in the uterus, they can lead to infections that can result in metritis. This can have a significant impact on the health of the postpartum cow.

Previous methods for removing dead tissue from the uterus of dairy cows have used liquid hydrogen peroxide. See U.S. Pat. No. 3,903,265. Such methods, however, are difficult to perform properly and can be applied only under specific physiological conditions.

SUMMARY OF THE INVENTION

The invention directed to maintaining fertility or treating retained placenta, reproductive tract infection, or reproductive tract inflammation in an animal by administering carbamide peroxide to the reproductive tract of the animal. The administered carbamide peroxide cleanses the postpartum animal through foaming, proteolytic, and antimicrobial actions. The administered carbamide peroxide works itself into the spongy cotyledons and effervesces within the cotyledons' interstices. This foaming action applies a gentle pressure within the cotyledons that breaks loose the cotyledons from the uterine lining. The carbamide peroxide also provides an antiseptic action, likely through oxidative processes, that kills existing microorganisms and inhibits further microorganism growth within the confines of the reproductive tract. These combined actions effectively treat exiting cases of metritis or reduce occurrence of metritis in the postpartum animal. The administered carbamide peroxide safely degrades after expending its foaming proteolytic action and antimicrobial action and does not harm the animal or the animal's subsequent reproduction. Thus, the carbamide peroxide administration described herein improves fertility and allows for continued yield of animal products such as milk, with economic gain for the farmer.

A preferred version of the invention is a method of maintaining animal fertility while maintaining animal productivity. The method comprises administering an effective amount of a medicament comprising carbamide peroxide to a reproductive tract of an animal. The animal may be suspected of suffering from a retained placenta, reproductive tract infection, or reproductive tract inflammation such as metritis. In a preferred version of the invention, the animal is postpartum. Animals that may be administered the medicament include bovine, ovine, caprine, equine, and swine. The carbamide peroxide may be administered in a medicament taking a solid, a liquid, a gel, or a paste form. The medicament, for example, may comprise a bolus, a liquid flush, a loose powder, a hard-shelled capsule, a soft-shelled capsule, a gel, or a paste. The carbamide peroxide is preferably administered in an amount of from about 0.001 mg/kg body weight of the animal to about 10,000 mg/kg body weight of the animal. Preferred amounts include about 1 mg/kg body weight of the animal to about 200 mg/kg body weight of the animal. Alternatively or in addition, the carbamide peroxide may be administered in a discrete dose comprising about 0.1 g to about 25 g of carbamide peroxide. Preferred discrete doses include about 1.75 g or 3.5 g of carbamide peroxide. The 1.75-g dose is suitable, for example, for ovine, caprine, or swine, and the 3.5-g is suitable for bovine or equine. The carbamide peroxide is preferably administered in one and only one discrete dose. A preferred formulation of the medicament is a bolus including about 3.5 g carbamide peroxide per bolus. Such a bolus can be administered directly in whole or in part or can be dissolved in a solvent to generate a flush for administration. In addition to carbamide peroxide, the administered medicament may further include an essential oil or an antibiotic, although it is preferred that the medicament is devoid of antibiotics.

The objects and advantages of the invention will appear more fully from the following detailed description of the preferred embodiment of the invention.

DETAILED DESCRIPTION OF THE INVENTION

The invention includes administering a medicament comprising carbamide peroxide to an animal. Carbamide peroxide is a white crystalline solid with the molecular formula $CH_6N_2O_3$, $(CH_4N_2O.H_2O_2)$. Carbamide peroxide is also called urea peroxide, urea hydrogen peroxide, and percarbamide. It is an oxidizing agent that releases oxygen in contact with water. Carbamide peroxide is an adduct of hydrogen peroxide and urea. An adduct is a product of a direct addition of two or more distinct molecules, resulting in a single reaction product containing all atoms of all components. The resultant adduct is considered a distinct molecular species from each of the molecular entities from which it is formed (see IUPAC, Compendium of Chemical Terminology, 2nd ed. (the "Gold Book") (1997)).

The medicament comprising carbamide peroxide may consist of carbamide peroxide or may include carbamide peroxide with other ingredients. The medicament may take any of a number of forms. Such forms include solid boluses, liquid flushes, loose powders, gelatin capsules, gels, or pastes. The boluses, loose powders, and gelatin capsules are solid forms. The liquid flushes are liquid forms. A preferred amount of carbamide peroxide in the medicament is an amount of from about 0.1 to about 25 g, such as about 3.5 g.

A preferred bolus formulation comprises a mixture of 38.89 parts of carbamide peroxide, 26.78 parts microcrystalline cellulose, 33 parts corn starch, 100 parts dicalcium phosphate, 0.33 parts FD&C blue #2 (Parchem, New Rochelle, N.Y.), and 1 part magnesium stearate. The mixture is pressed into 15-through 18-gram boluses using standard bolus-making equipment. Other proportions or including other binder ingredients or fillers is acceptable. The total size (mass) of the bolus can be larger or smaller depending on the needs of the user.

Flushes can be made by dissolving carbamide peroxide in a pharmaceutically acceptable solvent, such as water or any number of buffered solutions known in the art. A preferred flush is made by dissolving one or more boluses in warni water. A preferred ratio is 2 boluses per pint of water. This ratio is preferred for administration to bovines. The ratio of bolus to water and the total volume of the flush can be adjusted according to the size of the animal.

Loose powders may comprise crushed carbamide peroxide crystals. Such powders may additionally comprise fillers or anti-caking agents known in the art. A preferred powder comprises crushed boluses.

Two main types of gelatin capsules include hard-shelled capsules and soft-shelled capsules. Hard-shelled capsules are normally used for dry, powdered ingredients, miniature pellets, or spheroids (Caleva Process Solutions, Dorset, UK). Soft-shelled capsules are primarily used for liquids or for dry active ingredients that are dissolved or suspended in oil or other liquids. Both of these classes of capsules are made from aqueous solutions of gelling agents. Examples of suitable gelling agents include animal protein, such as gelatin, and plant polysaccharides or their derivatives, such as carrageenans or modified forms of starch or cellulose. Other ingredients can be added to the gelling agent solution. These include plasticizers such as glycerin and/or sorbitol to decrease the capsule's hardness, coloring agents, preservatives, disintegrants, lubricants, and surface treatments.

Gels or pastes comprising carbamide peroxide are well known in the art for teeth-whitening applications. These pastes and gels are suitable for use in the present invention. The concentration of carbamide peroxide in the paste or gel is preferably in a range of from 20-80%. Other concentrations are acceptable.

As is apparent from the foregoing, the medicament comprising carbamide peroxide may further comprise other ingredients. The other ingredients may be effective or inert. Examples of effective ingredients include those that help reduce infection. These include essential oils and other plant-based oils and compounds. Examples of suitable essential oils include oregano, garlic, thyme, rosewood, celery seed, frankincense, yiang yiang, cedarwood, lime, orange, petitgrain, bergamot, lemon, grapefruit, mandarin, myrrh, coriander, pumpkin, cypress, lemongrass, palmarosa, citronella, carrot seed, eucalyptus, fennel, wintergreen, juniper, French lavender, Tasmanian lavender, macadamia, tea tree, cajuput, niaouli, peppermint, spearmint, basil, evening primrose, marjoram, geranium, aniseed, bay, pine, black pepper, patchouli, apricot kernel, sweet almond, rosemary, sage, clary sage, sandalwood, clove, vetiver, and ginger oils. Other effective ingredients include traditional antibiotics, such as oxytetracycline, if desired for further efficacy. However, medicaments including traditional antibiotics may require withholding of milk after administration. Yet another effective ingredient that may be included in the medicament is prostaglandin.

Examples of inert ingredients that may be included in the medicament include any of the ingredients listed above as being included in the boluses, liquid flushes, loose powders, gelatin capsules, gels, or pastes. Other examples of inert ingredients include those known in the art of generating pharmaceutical formulations.

The methods of administering carbamide peroxide described herein can be used to maintain fertility in an animal. The administered carbamide peroxide protects against or treats conditions that cause infertility in an animal, such as retained placenta, reproductive tract infection, or reproductive tract inflammation. The word "maintain," used in the context of maintaining fertility, refers to both preservation of fertility in a fertile animal or reversal of infertility due to retained placenta, reproductive tract infection, or reproductive tract inflammation in a previously fertile animal.

The methods of administering carbamide peroxide described herein can also be used to maintain animal fertility while maintaining animal productivity. As used in this context, "productivity" refers to the ability of the animal to produce a good or product. For example, if the animal is a milk producer, the carbamide peroxide administration enables the animal to continue milk production. If the animal is used for its meat, the carbamide peroxide administration enables the meat to be used after administration.

It is preferable that the carbamide peroxide is administered in a manner that maintains animal fertility while allowing for continued production of animal products suitable for human use or consumption. For example, the methods of administering carbamide peroxide described herein are effective in maintaining fertility without administration of antibiotics, the latter of which renders the animal's milk unsuitable for sale for human consumption. In some cases, the carbamide peroxide treatment may be combined with antibiotics. However, the dose of antibiotics in such cases can be greatly reduced compared to administration in the absence of carbamide peroxide.

The methods described herein include administering carbamide peroxide to the reproductive tract of an animal. As used herein, "reproductive tract" refers to any of an animal's vulva, vestibule, vagina, cervix, or uterus. For example, carbamide peroxide can be administered to any of these parts of the reproductive tract for treatment of infection therein. For uses in maintaining fertility, it is preferred that the carbamide peroxide is administered intrauterally, i.e., in the uterus.

The carbamide peroxide administration described herein is effective to protect against or treat cases of retained placenta. As used herein, "retained placenta" refers to retention of the placenta, whether the whole placenta or fragments thereof, in the uterus or reproductive tract. In protecting against retained placenta, the carbamide peroxide is administered to a postpartum animal, whether showing signs of retained placenta or not. The carbamide peroxide can be administered any time after parturition. Examples include administering the carbamide peroxide the day of parturition or within about 1, 2, 3, 4, 5, 7, 10, 15, or 30 or more days after parturition. To treat retained placenta, the carbamide peroxide is administered to a postpartum animal suspected of—or confirmed as—suffering from a retained placenta. To determine if an animal may be suffering from a retained placenta, the placenta (afterbirth) may be inspected to determine whether or not it is primarily intact. A placenta that is not primarily intact may indicate retained placental fragments in the reproductive tract. Another sign of retained placenta is infertility in a postpartum animal. Other signs of retained placenta are known in the art.

The carbamide peroxide administration described herein is also effective to protect against or treat reproductive tract infection. Reproductive tract infection is a major cause of infertility. Reproductive tract infection itself has many disparate causes, one of which is retained placenta. The carbamide peroxide may protect against or treat reproductive tract infection that is secondary to retained placenta or that is independent of, or occurs in the absence of, retained placenta. The carbamide peroxide may be used to protect against or treat infection in any part of the reproductive tract as described herein, including the vulva, vestibule, vagina, cervix, or uterus. Protecting against reproductive tract infection occurs through periodic carbamide peroxide administration, whether or not reproductive tract infection is suspected. Treatment of reproductive tract infection occurs through carbamide peroxide administration when reproductive tract infection is either confirmed or suspected. Indicators of reproductive tract infection include purulence within the reproductive tract, purulent vaginal discharge, or positive identification of microbial infection from cultures of the reproductive tract. Carbamide peroxide administration can protect against or treat infections with such microorganisms as bacteria, protozoa, and fungi. Examples of bacteria that are susceptible to carbamide peroxide treatment include Clostridia, *Fusobacterium necrophorum*, *Bacteriodes melaninogenicus*, *Bacteriodes fragillus*, *Actinomyces pyogenes*, *Ureaplasma* such as *Ureaplasm diversum*, *Mycoplasma* such as *Mycoplasma bovigenitalium* and *Mycoplasma bovigenitalium*, *Hemophilus somnus*, and *Campylobacter*. An example of a protozoan that is susceptible to carbamide peroxide treatment is Trichomonal foetus.

The carbamide peroxide administration described herein is also effective to protect against or treat reproductive tract inflammation, particularly inflammation resulting from reproductive tract infection. Like reproductive tract infection, reproductive tract inflammation is another major cause of infertility. The carbamide peroxide may be used to protect against or treat inflammation of any part of the reproductive tract as described herein, including the vulva, vestibule, vagina, cervix, or uterus. Examples include vulvitis, vestibulitis, vaginitis, cervicitis, and metritus or endometritis. Protecting against reproductive tract inflammation occurs through periodic carbamide peroxide administration, whether or not reproductive tract inflammation is suspected. Treatment of reproductive tract inflammation occurs through carbamide peroxide administration when reproductive tract inflammation is either confirmed or suspected. Indicators of reproductive tract inflammation include redness or swelling of the affected portion of the reproductive tract.

A preferred version of the invention comprises administering carbamide peroxide to protect against or treat metritis (inflammation of the uterus). One form of metritis involves inflammation of the endometrium (the lining of the uterus), the underlying glandular tissues, and the muscular layers. Another form of metritis, called "endometritis," involves inflammation of only the endometrium and the underlying glandular tissues. Commonly, "metritis" is used to indicate both forms and is used accordingly herein. A clinical or subclinical form of metritis may be present. Carbamide peroxide is effective in treating both types.

Clinical metritis may be either acute, i.e., appearing quickly and generally affecting the cow's appetite and milk production, or chronic, i.e., persisting over a long period of time. Clinical metritis can be diagnosed by the presence of a purulent vaginal discharge. This diagnosis should be confirmed by a veterinarian on rectal palpation. Further diagnostic techniques such as vaginal examination, uterine culture, or biopsy may be necessary. The criteria noted on palpation and vaginal exam include the size of the uterus as related to time of calving, thickness of the wall of the uterus and the presence, color, odor and consistency of fluid draining from one or both horns. A history of calving trauma, dystocia (difficult calving), retained placenta, or a purulent vaginal discharge during the post-calving period supports the diagnosis of metritis. The presence of pus as observed by an inseminator may indicate possible inflammation of the uterus. However, small amounts of pus-like material on the insemination pipette and whitish vulvar discharges within 12 to 24 hours following natural breeding are not necessarily signs of metritis, as inflammation of the cervix (cervicitis) and vagina (vaginitis) also produce abnormal discharges. Unless fluid can be palpated in the uterus, further examination using a vaginal speculum is recommended. Diagnosis of clinical metritis can be confirmed by a uterine biopsy. Microscopic examination of the biopsy tissue can reveal the presence of acute or chronic inflammation of the uterine wall as well as other abnormalities. The uterine biopsy is especially valuable in assessing the repeat breeder's future reproductive potential. Simultaneous biopsy sampling and uterine cultures can positively confirm the presence of metritis and the presence or absence of organisms in the uterus (i.e., uterine infection).

Other signs that may indicate a suspected case of clinical metritis include infertility uterine atony or inertia, systemic illness, depression, anorexia, gastrointestinal atony, agalactia, fever, peritonitis, and fetid, foul-smelling, watery, and reddish-black uterine discharge.

Subclinical metritis more commonly occurs in the chronic rather than the acute form. Subclinical metritis is not detectable by rectal palpation. No vaginal discharge is evident. Sometimes examination with a speculum will reveal a purulent discharge, but not always. Cultures of the uterus may or may not verify a microbial infection. For example, many times the repeat breeder is negative on culture. However, subclinical endometritis can be positively diagnosed by microscopic examination of a uterine biopsy. A sign that may indicate a suspected case of subclinical metritis is infertility.

Whether acute, chronic, clinical or subclinical, metritis often results from reproductive tract infection. A large number of microorganisms have been implicated as causes of metritis. Bacteria, fungi, and protozoa have been cultured from uteri when metritis has been present. Microorganisms enter the uterus through several routes. Most commonly, the microorganisms contaminate the uterus during calving or the early post-calving period. The reproductive tract is very susceptible at this time, especially if trauma or lesions in the vagina or vulva are present and the animal's natural defenses are lowered. Any assistance or manipulations performed during parturition can easily introduce microorganisms into the uterus. Infection in the uterus may also result from an infection elsewhere in the body such as systemic infections, which then spread to the uterus. This can occur, for example, with infection with *Leptospira interrogans* (Leptospirosis). Microorganisms also can enter the reproductive tract during natural breeding with a bull via a venereal route. The two most common venereal diseases are campylobacteriosis (vibriosis) and trichomoniasis. Infection can be transmitted either by an infected bull or carried by the bull to a susceptible female from an infected female. Semen-borne infections are less common types of infections. However, these infections can be dangerous if cows are inseminated when not in estrus. The resistance of the uterus to infection is much lower during the period of non-estrus as compared to during estrus. Certain organisms such as *Ureaplasmas*, *Mycoplasmas*, and *Hemophilus somnus* are common inhabitants of the vagina and can cause metritis. These organisms appear to be a more common cause of metritis in parts of the country than other causes listed previously.

In some cases, certain infectious bacteria can have synergistic relationships in the uterus and lead to metritis. For example, *Fusobacterium necrophorum* produces a leucotoxin, and *Bacteriodes melaninogenicus* and *fragillus* produce and release a substance which prevents phagocytosis. These mechanisms adversely affect the animal's immune defenses and thereby render the animal susceptible to infection with other microbes. In addition, *Actinomyces pyogenes* produces a growth factor for such bacteria as *Fusobacterium*. Therefore, *A. pyogenes* is particularly harmful. *A. pyogenes* causes extensive damage if present for greater than one week. After clearing the uterus of *A. pyogenes* it takes at least 1 month to resolve the damage and restore fertility. The carbamide peroxide administration described herein is effective in treating metritis or other inflammations of the reproductive tract, in part, by treating these underlying microbial infections.

The carbamide peroxide administration described herein can be used to maintain fertility, maintain productivity, or treat any of the conditions described herein in any animal having a reproductive tract that is susceptible to the conditions described herein. Preferred examples of such animals include mammals in general and, more specifically, bovines, ovines, caprines, equines, swine, and humans. Expressly included among bovines are dairy cows, beef cows, and buffalo. Ruminants are particularly preferred for carbamide peroxide administration.

The carbamide peroxide or medicament comprising same is administered to the animal in an effective amount. "Effective amount" as used herein refers to an amount of carbamide peroxide capable of protecting against or treating retained placenta, infection of the reproductive tract, or inflammation of the reproductive tract in a given animal, such that animal fertility is maintained and/or animal productivity is maintained. The effective amount may vary on a case-by-case basis. Factors to consider in determining an effective amount include the weight of the animal and the degree of the condition, if any, from which it suffers or is suspected of suffering. For example, a threshold effective amount in protecting against retained placenta, reproductive tract infection, or reproductive tract inflammation is typically much less than the threshold effective amount in an animal that is confirmed or suspected of suffering from one of these conditions. The threshold effective amount is also less in lower-weight animals than higher-weight animals, the weight of the animal generally reflecting the size of the reproductive tract.

In general, a preferred effective amount of carbamide peroxide administered to an animal comprises an amount of carbamide peroxide no less than about 0.001 mg/kg, no less than about 0.01 mg/kg, no less than about 0.1 mg/kg, or no less than about 1 mg/kg. As used herein, "mg/kg" refers to mg carbamide peroxide per kilogram body weight of the animal. A preferred effective amount of carbamide peroxide comprises an amount of carbamide peroxide no more than about 10,000 mg/kg, no more than about 1,000 mg/kg, no more than about 500 mg/kg, or no more than about 200 mg/kg body weight. Preferred effective ranges include from about 0.001 mg/kg to about 10,000 mg/kg, from about 0.1 mg/kg to about 1,000 mg/kg, or about 1 mg/kg to about 200 mg/kg.

The effective amount of the carbamide peroxide can be administered in one or more discrete doses. As used herein, "dose" refers to the amount of carbamide peroxide administered at one time. The discrete dose is preferably in an amount of from about 0.1 g to about 25 g of carbamide peroxide, and more preferably in an amount of from about 1 g to 10 g carbamide peroxide. Greater or lesser amounts may be used in specific cases. Particularly preferred discrete doses include about 3.5 g or about 1.75 g carbamide peroxide. The discrete dose can be formulated in any of the medicament forms described herein. Formulating the carbamide peroxide in boluses, liquid flushes, loose powder, gels, or pastes is particularly convenient for administering the medicament in an appropriate discrete dose, as such medicament forms can be broken down, subdivided, and/or combined into discrete doses suitable for a variety of different animals. For example, a medicament form such as a bolus comprising a discrete dose suitable for a bovine or an equine may be divided into individual, discrete doses suitable for ovine, caprine, or swine by breaking the bolus into a half or thirds, etc.

It is preferred that the effective amount of the carbamide peroxide is administered in a single discrete dose. Single discrete doses minimize the risks associated with multiple administrations, such as aggravating infection or introducing other pathogens into the reproductive tract. The single discrete doses are preferably in an amount of from about 0.1 g to about 25 g of carbamide peroxide, and more preferably in an amount of from about 1 g to 10 g carbamide peroxide. A single discrete dose of about 3-4 g carbamide peroxide, such as about 3.5 g carbamide peroxide, is suitable for bovines or equines. A single discrete dose of about 0.5-1 g carbamide peroxide, such as about 1.75 g carbamide peroxide, is suitable for ovine, caprine, and swine.

The medicament comprising the carbamide peroxide is preferably devoid of agents such as antibiotics (oxytetracycline, nitrofurazone, or metronidazole) and/or prostaglandin that may appear in the animal's milk. Milk or other animal products therefore do not have to be withheld by the farmer during or after administration of the medicament. Accordingly, some versions of the invention comprise collecting animal products suitable for human consumption from the animal during and/or after the carbamide peroxide administration. The animal products can be collected any time after administration, including one day, two days, three days, one week, two weeks, or one month after administration. Examples of animal products include meat, milk, etc. As used herein, "suitable for human consumption" refers to animal products devoid of antibiotics or human toxins.

A preferred version of the invention uses a bolus comprising about 3.5 g carbamide peroxide and devoid of such drugs as antibiotics or prostaglandin. Treatment preferably occurs by administering a single bolus or fragment thereof corresponding to a single discrete dose for the particular animal. This can be followed by administration of a second bolus or fragment thereof, if needed. Alternatively, the bolus or fragment thereof corresponding to the single discrete dose may be dissolved in a pint of warm water, which is then used as a liquid flush for cleaning the uterus of postpartum animals (such as cows) or for treating known or suspected cases of retained placenta, reproductive tract infection, or reproductive tract inflammation such as metris. The invention physically removes any retained placental debris, kills bacteria responsible for metris, and thus encourages regeneration of healthy uterine environment. This accelerates recovery from uterine infection, minimizes postpartum risk factors for reproduction tract inflammation such as metris, and/or treats current cases of reproductive tract inflammation. Because the administered bolus or flush non-medicated, there is no need for milk or other animal product withholding by the farmer, thus increasing profits.

The elements and method steps described herein can be used in any combination whether explicitly described or not. All combinations of method steps as described herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls.

The methods, compounds, and compositions of the present invention can comprise, consist of, or consist essentially of the essential elements and limitations described herein, as well as any additional or optional steps, ingredients, components, or limitations described herein or otherwise useful in the art.

It is understood that the invention is not confined to the particular construction and arrangement of parts herein illustrated and described, but embraces such modified forms thereof as come within the scope of the claims.

The following examples show how the invention effectively kills metris-causing organisms both in vitro and in vivo and safely eliminates retained placenta in cows.

Example 1

In vitro testing: One-ml aliquots of uterine discharge from a cow with confirmed metris were collected and diluted with 1 ml of water. The aliquots were incubated for 30 minutes at 37° C. either in the presence of 7.0% carbamide peroxide (test) or in the absence of carbamide peroxide (control). Bacteria from each treatment were washed and centrifuged, reconstituted in media, and plated on suitable culture media plates. The plates were incubated for three days. While hundreds of bacteria colonies were enumerated in the control plates, no colonies were found in the test plates. This indicated that carbamide peroxide effectively kills metris-causing organisms in vitro. A similar experiment was conducted using urea in place of carbamide peroxide. The concentration of urea used was 11.3%. This is the equivalent amount of urea found in 4 urea boluses per 16 ounces of water, which is recommended for in vivo treatment using commercially available urea boluses. The urea treatment resulted in several bacterial colonies still being present. This indicated that the carbamide peroxide was more effective than urea in killing metris-causing organisms.

Example 2

Efficacy of carbamide peroxide administration in treating retained placenta was tested in clinical trials with cows having retained placenta. A single bolus containing 3.5 grams carbamide peroxide was inserted in the uterus of postpartum cows with retained placenta. The next day, the retained placenta was shed naturally. There was no foul uterine discharge that would have been expected with complications arising from the retained placenta. This indicated that the carbamide peroxide treatment effectively caused the retained placenta and placental remnants to be shed in a timely manner.

Example 3

Efficacy of carbamide peroxide administration for treating metris was tested in clinical trials with cows diagnosed with metris. A single bolus containing 3.5 grams carbamide peroxide was inserted in the uterus of cows showing metris symptoms such as foul uterine discharge. The discharge improved and reduced quickly. The treated cows did not go off feed during the treatment and were able to rejoin normal herd operations. No follow-up with antibiotics were required in these animals, indicating that the carbamide peroxide administration had resolved the metris symptoms. As no antibiotics were required in these cases, no milk had to be discarded. Because no milk was discarded, full financial benefit to the farmer was received for selling more milk than would have occurred if milk had to be discarded due to the presence of antibiotics. Cows that received the carbamide peroxide treatments subsequently conceived safely and had healthy calves. This indicates the carbamide peroxide administration is safe for use for the long term health of the cow and helps reduce subsequent reproduction failures.

Example 4

Efficacy of carbamide peroxide administration in a wash format was tested with a cow diagnosed with severe metritis and vaginitis. A cow that had calved 5 days previously presented a foul smelling uterine discharge. Upon clinical examination, it was discovered that remnants of the placenta were still in the uterus and that the animal was off feed. Antibiotics were not preferred for treatment, as sale of milk from the cow was very important. (Antibiotic residue in milk is not permitted if sale of milk is to occur.) Two boluses comprising 3.5 g carbamide peroxide were dissolved in 1 quart of water, and the uterus of the cow was flushed out with the flush. Within 24-48 hours, the uterine discharge had cleared, the cow was on feed again, and placental remnants were gone. The animal was able to be milked easier than prior to treatment, and the cow was returned to normal service in good health. As no antibiotics were used, the milk was not required to be discarded, and the owner was able to make financial gain from the sale of the milk.

While this invention may be embodied in many forms, what is described in detail herein is a specific preferred embodiment of the invention. The present disclosure is an exemplification of the principles of the invention is not intended to limit the invention to the particular embodiments illustrated. It is to be understood that this invention is not limited to the particular examples, process steps, and materials disclosed herein as such process steps and materials may vary somewhat. It is also understood that the terminology used herein is used for the purpose of describing particular embodiments only and is not intended to be limiting since the scope of the present invention will be limited to only the appended claims and equivalents thereof.

We claim:

1. A method of treating an animal that is suspected of suffering from metritis, retained placenta, reproductive tract infection, or reproductive tract inflammation comprising administering an effective amount of a medicament comprising carbamide peroxide to a reproductive tract of the animal, wherein the medicament is administered in a solid form, wherein the solid form is a solid bolus or a loose powder.

2. The method of claim 1 wherein the animal is postpartum.

3. The method of claim 1 wherein the animal is selected from the group consisting of bovine, ovine, caprine, equine, and swine.

4. The method of claim 1 wherein the medicament is administered in a dose comprising an amount of about 0.1 g to about 25 g of carbamide peroxide.

5. The method of claim 4 wherein the dose consists in about 1.75 g or 3.5 g of carbamide peroxide.

6. The method of claim 1 comprising administering a single dose of the medicament.

7. The method of claim 6 wherein the animal is bovine or equine and the dose is about 3.5 g.

8. The method of claim 6 wherein the animal is ovine, caprine, or swine and the dose is about 1.75 g.

9. A method of treating an animal that is suspected of suffering from metritis, retained placenta, reproductive tract infection, or reproductive tract inflammation comprising administering an effective amount of a medicament comprising carbamide peroxide to a reproductive tract of the animal, wherein the medicament is administered in a solid form, the administering comprising administering a solid bolus or portions thereof, wherein the bolus includes about 3.5 g carbamide peroxide per bolus.

10. The method of claim 1 comprising administering the carbamide peroxide in an amount of from about 0.001 mg/kg body weight of the animal to about 10,000 mg/kg body weight of the animal.

11. The method of claim 1 comprising administering the carbamide peroxide in an amount of from about 1 mg/kg body weight of the animal to about 200 mg/kg body weight of the animal.

12. The method of claim 1 further comprising, after the administering, collecting milk suitable for human consumption from the animal.

* * * * *